(12) United States Patent
Chen et al.

(10) Patent No.: US 11,590,180 B2
(45) Date of Patent: Feb. 28, 2023

(54) BIFIDOBACTERIUM LACTIS GKK2, A COMPOSITION COMPRISING THEREOF AND ITS USE FOR IMPROVING ALLERGIC ASTHMA

(71) Applicant: GRAPE KING BIO LTD., Taoyuan (TW)

(72) Inventors: Chin-Chu Chen, Taoyuan (TW); Yen-Lien Chen, Taoyuan (TW); Shin-Wei Lin, Taoyuan (TW); Yen-Po Chen, Taoyuan (TW); Ci-Sian Wang, Taoyuan (TW); Yu-Hsin Hou, Taoyuan (TW); Yang-Tzu Shih, Taoyuan (TW); Ching-Wen Lin, Taoyuan (TW); Ya-Jyun Chen, Taoyuan (TW); Jia-Lin Jiang, Taoyuan (TW)

(73) Assignee: GRAPE KING BIO LTD., Taoyuan (TW)

( * ) Notice: Subject to any disclaimer, the term of this patent is extended or adjusted under 35 U.S.C. 154(b) by 66 days.

(21) Appl. No.: 16/541,964

(22) Filed: Aug. 15, 2019

(65) Prior Publication Data
US 2020/0054691 A1 Feb. 20, 2020

(30) Foreign Application Priority Data
Aug. 16, 2018 (TW) ................................ 107128653

(51) Int. Cl.
| | |
|---|---|
| *A61P 11/06* | (2006.01) |
| *A61P 37/08* | (2006.01) |
| *A61K 35/745* | (2015.01) |
| *A23L 33/135* | (2016.01) |
| *A61K 9/19* | (2006.01) |
| *A23L 2/52* | (2006.01) |

(52) U.S. Cl.
CPC .............. *A61K 35/745* (2013.01); *A23L 2/52* (2013.01); *A23L 33/135* (2016.08); *A61K 9/19* (2013.01); *A61P 11/06* (2018.01)

(58) Field of Classification Search
CPC .. A61K 35/745; A61K 9/19; A61K 2035/115; A23L 33/135; A23L 2/52; A23L 2/382; A23L 2/84; C12N 1/20; A23K 10/18; A23V 2002/00; A23Y 2300/49; A61P 11/06; A61P 37/08
See application file for complete search history.

(56) References Cited

U.S. PATENT DOCUMENTS

2016/0303226 A1* 10/2016 Mercenier .............. A23C 9/123

FOREIGN PATENT DOCUMENTS

CA 2969604 A1 * 8/2016 ........... A61K 35/745

OTHER PUBLICATIONS

Othman et al. Strategies for improving production performance of probiotic Pediococcus acidilactici viable cell by overcoming lactic acid inhibition. AMB Expr. 2017;7:215 1-14.*

* cited by examiner

*Primary Examiner* — Lynn Y Fan
(74) *Attorney, Agent, or Firm* — Birch, Stewart, Kolasch & Birch, LLP (57) ABSTRACT

The present invention provides a *Bifidobacterium lactis* GKK2, a composition comprising thereof and its use for improving asthma, especially for lowering airway resistance, reducing levels of non-specific and specific IgE in serum, alleviating bronchoconstriction and increasing levels of GSH reductase in liver tissue interstitial fluid to improve allergic asthma.

14 Claims, 5 Drawing Sheets

BIFIDOBACTERIUM LACTIS GKK2, A COMPOSITION COMPRISING THEREOF AND ITS USE FOR IMPROVING ALLERGIC ASTHMA

BACKGROUND

Technical Field

The present invention relates to a lactic acid bacteria, a composition comprising thereof and its use for improving allergic asthma. More specifically, the present invention relates to a composition comprising *Bifidobacterium Lactis*, the method for manufacturing the bacteria, and the use of this bacteria to lower airway resistance, reduce non-specific and specific IgE levels in serum, relieve bronchoconstriction, increase GSH reductase levels in liver tissue interstitial fluid when administered to a subject, thereby improving allergic asthma.

Description of Related Art

Allergic Responses

An allergic response is a hypersensitive immune reaction to a substance that is normally harmless. Such response may further cause harmful symptoms such as acute or chronic inflammation, or even organ dysfunction in more serious cases. Common allergic diseases include allergic asthma, allergic rhinitis, hives, and atopic dermatitis.

Allergic Asthma

Allergic asthma is a disease of the respiratory tract, whose prevalence continues to rise along with global environmental degradation. The most common signs of allergic asthma include difficulty breathing, coughing, tightness in the chest and wheezing. Such disease may be fatal in more serious cases. Upon entering into the human body by various means, environmental allergens first undergo the process of sensitization. In other words, allergens bind to an antigen-specific cell as soon as they contact the human body. Next, the antigen-specific cell presents the allergens to T-lymphocytes, which then differentiate into Th2 cells and release various inflammatory cytokines. At the same time, B-lymphocytes are activated by the allergens to produce IgE antibodies (Immunoglobulin E). IgE antibodies enter tissues through blood flow and bind to mast cell surfaces, thereby making the individual predisposed to allergic responses. When the human body is exposed to the same allergens again, the allergens will bind to the IgE antibodies located on the mast cell surfaces, and the mast cells will be activated to release inflammatory cytokines, such as histamine, leukotriene (LT), interleukin (IL), which directly or indirectly cause inflammatory responses in the respiratory tract. As these responses occur, the air passages will swell and the smooth muscles around them will contract, resulting in airway narrowing. When the airway is filled with accumulated mucus secreted from mucous glands, abrupt airway contraction followed by asthma will occur.

Glutathione

Glutathione (GSH) is a tripeptide composed of glutamic acid, cysteine and glycine with γ-amide linkages and thiol moieties. GSH is present in almost all cell strains and can help maintain normal immune functions. GSH reductase can reduce GSSG to GSH and thereby increase the levels of GSH in the body in order to strengthen the immune system.

*Bifidobacterium*

*Bifidobacterium* is a genus of gram-positive, nonmotile, rod-shaped and often branched anaerobic bacteria. They are ubiquitous inhabitants of the gastrointestinal tract, vagina and mouth of human and animals. In 1899, they were first isolated from feces of healthy infants, and it was later discovered that certain *Bifidobacterium* strains can be used as probiotics to be added in foods, medicine and feeds.

Studies suggested that certain lactic acid bacteria strains may increase the expression of IFN-γ and reduce the expression levels of allergy-related IL-4, IL-5 and specific IgE, thereby down-regulating Th2 immune responses and alleviating allergic responses. Other studies suggested that feeding lactic acid bacteria for 4 consecutive months may increase IFN-γ secretion in people predisposed to allergies and improve their allergic symptoms. In recent years, there have been clinical studies showing that early feeding of probiotics may help alleviate symptoms and reduce outbreaks of atopic dermatitis in breast-fed infants, thereby reducing outbreaks of allergic asthma accordingly. In addition, scholars conducted double-blind studies using *L. acidophilus* and found that *L. acidophilus* are useful in alleviating symptoms of allergic asthma associated with dust mites and pollens. However, none of the bacteria mentioned above are able to relieve airway hyperconstriction.

SUMMARY

The present invention provides a *Bifidobacterium lactis*, which is acid-tolerant, bile-tolerant and/or heat-tolerant. The colony forming unit per milliliter is about $5 \times 10^8$ cfu/ml in a culture medium at pH 3.2 to 2.0, about $5 \times 10^9$ cfu/ml in a liquid culture mixed with 0.3% bile salt, and/or $5 \times 10^7$ to $5 \times 10^9$ cfu/ml in a liquid culture heated at a desired temperature for 0 to 15 minutes.

Preferably, the strain is *Bifidobacterium lactis* GKK2, and is deposited (CGMCC No. 15205) at China General Microbiological Culture Collection Center.

The present invention provides a composition for improving allergic asthma, which comprises a *Bifidobacterium lactis* GKK2. The strain is deposited (CGMCC No. 15205) at China General Microbiological Culture Collection Center.

The present invention also provides a composition for improving allergic asthma, which comprises an active substance of *Bifidobacterium lactis* GKK2. GKK2 is deposited (CGMCC No. 15205) at China General Microbiological Culture Collection Center.

Preferably, the active substance is prepared by the following method:
 (a) Streaking bifidobacterial strains onto the agar plate to produce single colonies; and
 (b) Inoculating a single colony of lactic acid bacteria cultured at step (a) to a liquid culture for liquid-state culture.

Preferably, the method further comprises the following steps:
 (c) Centrifuging the liquid culture that was cultured at step (b) to obtain a bacterial pellet; and
 (d) Freeze-drying the bacterial pellet obtained at step (c).

Preferably, step (b) is carried out at 30 to 50° C., in nitrogen or carbon dioxide of 0 to 1 vvm, rotate at 10 to 100 rpm, and/or incubate for 16 to 24 hours.

Preferably, the temperature for the freeze-drying at step (d) is −196 to −40° C.

Preferably, the composition includes an additive selected from the group consisting of an excipient, preservative, diluent, filler, absorption enhancer, sweetener and a combination thereof.

Preferably, the composition is a drug, feed, drink, nutritional supplement, dairy product or health food.

Preferably, the composition takes the form of a powder, tablet, granule, suppository, microcapsule, ampoule/ampule, liquid spray or suppository form.

The GKK2 strain of the present invention has been manufactured and proven to improve allergic asthma.

Preferably, in terms of the method for improving allergic asthma, a subject having been administered the GKK2 strain exhibits lower airway resistance than a subject not administered the GKK2 strain.

Preferably, in terms of the method for improving allergic asthma, a subject having been administered the GKK2 strain exhibits reduced levels of non-specific IgE antibodies in serum than a subject not administered the GKK2 strain.

Preferably, in terms of the method for improving allergic asthma, a subject having been administered the GKK2 strain exhibits reduced levels of specific IgE antibodies in serum than a subject not administered the GKK2 strain.

Preferably, in terms of the method for improving allergic asthma, a subject having been administered the GKK2 strain exhibits less bronchoconstriction than a subject not administered the GKK2 strain.

Preferably, in terms of the method for improving allergic asthma, a subject having been administered the GKK2 strain exhibits increased levels of GSH reductase in liver tissue interstitial fluid than a subject not administered the GKK2 strain.

DETAILED DESCRIPTION

Source of Lactic Acid Bacteria

The lactic acid bacteria used in the present invention are *Bifidobacterium lactis* of the *Bifidobacterium* genus. In a preferred embodiment, the lactic acid bacteria are isolated from the fecal samples collected from healthy male breast-fed infants at three months of age, wherein the infants have never taken any medicine or been fed health foods since their birth, including probiotic supplements, which may affect gut functions and the microflora of the samples. These samples have a normal, mushy appearance in yellow color, which are in line with the characteristics of the stools of breast-fed babies. Once obtained, the samples are immediately stored in an anaerobic jar containing the AnaeroPack so that the anaerobic bacteria in the samples remain alive. Then the samples are immediately transported to the laboratory for isolation and screening of bacterial species. In a preferred embodiment, this bacteria species have successfully deposited in the Bioresource Collection and Research Center at Taiwan Food Industry Research and Development Institute (No. BCRC-910826) on Feb. 12, 2018 and in China General Microbiological Culture Collection Center (CGMCC; No. 15205) on Jan. 12, 2018 (Institute of Microbiology Chinese Academy of Sciences, No. 1 West Beichen Road Chaoyang District Beijing China).

Screening and Culture of GKK2

The anaerobic jar containing the samples is opened using an anaerobic workstation with an anaerobic environment. 2 grams of samples are gathered using a sterile sample spoon, and then homogenized in 200 ml of sterile saline. The homogenized samples are made into a $1:10^4 \sim 10^7$ dilution. The dilution is transferred onto a TOS-MUP culture medium using a pour plate method. Screening and isolation of *Bifidobacterium lactis* from the samples are performed using the TOS-MUP culture medium instead of the conventional BIM-25 culture medium as it has been proven to be more selective and without *Enterobacter* interference. The screening rate of *Bifidobacterium lactis* can be as high as 100%.

After culturing using the pour plate method, the plates are placed inside the anaerobic jar. The AnaeroPack is opened to absorb oxygen and the jar is sealed. The jar is then moved away from the anaerobic workstation and incubated in an incubator at 37±0.5° C. for 44-48 hours.

After incubation, the anaerobic jar is moved to the anaerobic workstation to be opened and for single strain selection and storage. More than 100 single colonies are selected from each sample for storage and examined using in vitro cell-based assays. Specifically, these in vitro assays are conducted using peripheral blood mononuclear cells, primary spleen cells and mast cells. Moreover, the CISD2 longevity gene in HEK293T cells was also examined. Using multiple in vitro assays, the strains that are screened and selected are high-potential lactic acid bacterial strains that can help boost immune system and alleviate allergic responses inside the body and on the skin. After selection, these novel probiotic strains can further be used for fermenting dairy products or fruit and vegetable juice, and for produced into probiotic powder that can be eaten directly, thereby improving various abnormal physiological responses.

Phenotypic Analysis

The lactic acid bacteria numbered 1 (GKK2) and other species are compared using acid tolerance, bile tolerance and heat tolerance tests to study phenotypic differences therebetween.

Acid Tolerance Test

Five species of strains, including GKK2, BCRC 17394 (purchased from the Bioresource Collection and Research Center at Taiwan Food Industry Research and Development Institute), *B. animalis* subsp. *Lactis* Bi 04 (deposited at the American Type Culture Collection, No. ATCC SD 5219), *B. animalis* subsp. *Lactis* BB-12 (deposited at the German Collection of Microorganisms and Cell Cultures, No. DSM 15954) and *B. animalis* subsp. *Lactis* Bi07 (deposited at the American Type Culture Collection, No. ATCC SD 5220) are used in this test. By adding HCl into the initial MRS liquid culture media, the pH level thereof is adjusted from about 6.5 to 3.2, 2.4 and 2.0. The strains are inoculated onto the culture media with different pH values and incubated for 3 hours at 37° C. The colonies formed are then counted.

Figure 1:
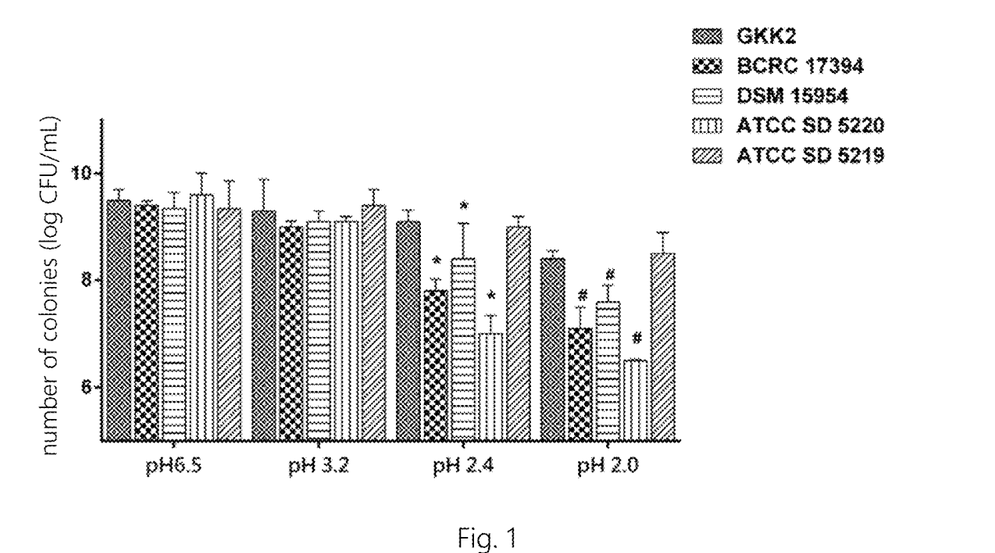
FIG. 1 shows the number of colonies after the acid tolerance test.

Results are shown in FIG. 1. At initial pH (about 6.5), the number of colonies of GKK2 and other four species all reached $5\times10^9$ cfu/ml. At pH 3.2, the number of colonies of all species reduced slightly without exhibiting any significant differences between GKK2 and other four species. When the pH level drops to 2.4 and 2.0, the number of colonies of BCRC 17394, BB-12 and Bi07 reduced to the $6^{th}$ and $7^{th}$ power, which are significantly lower than that of GKK2 maintained at $8^{th}$ power (p <0.05). As such, in acidic environment, the number of colonies of GKK2 is significantly greater than those of the other species. These results suggest that GKK2 are more acid-tolerant than the other species, and thus more resistant to gastric acid when passing through the stomach.

Bile Tolerance Test

Five species of strains, including GKK2, BCRC 17394 (purchased from the Bioresource Collection and Research Center at Taiwan Food Industry Research and Development Institute), *B. animalis* subsp. *Lactis* Bi 04 (deposited at the American Type Culture Collection, No. ATCC SD 5219), *B. animalis* subsp. *Lactis* BB-12 (deposited at the German Collection of Microorganisms and Cell Cultures, No. DSM 15954) and *B. animalis* subsp. *Lactis* Bi07 (deposited at the American Type Culture Collection, No. ATCC SD 5220) are used in this test. The strains are inoculated onto the MRS liquid culture media containing 0.3% bile salt and incubated for half an hour at 37° C. The colonies formed are then counted.

Figure 2:
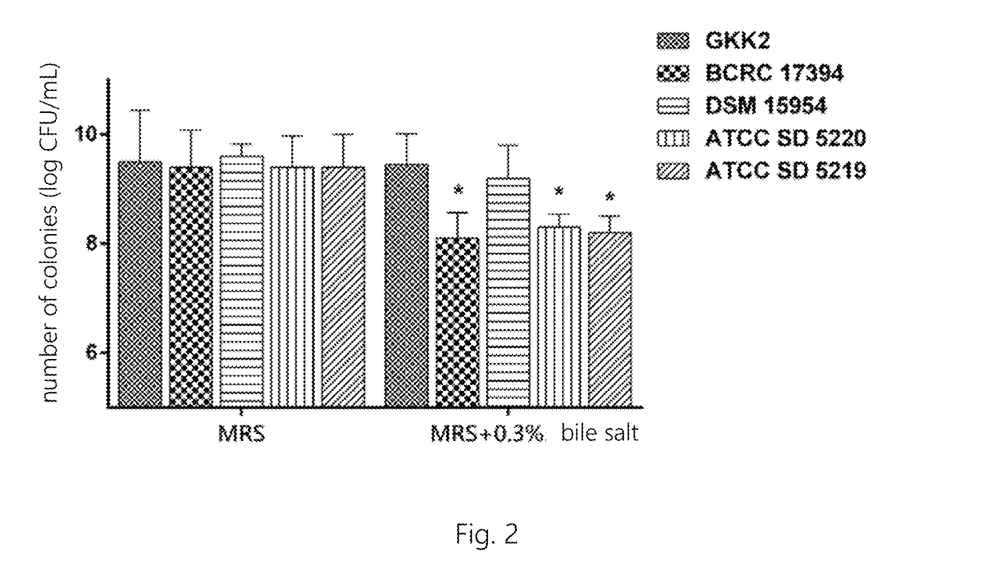
FIG. 2 shows the number of colonies after the bile salt tolerance test.

Results are shown in FIG. 2. The number of colonies of GKK2 and other four species all reached $5 \times 10^9$ cfu/ml at the initial MRS liquid culture media. On the other hand, the number of colonies of BCRC 17394, Bi04 and Bi07 are significantly lower than that of GKK2 ($p<0.05$) in the MRS containing 0.3% bile salt, while there is no statistically significant difference between the number of colonies of BB-12 and GKK2. As such, in an environment with bile salt, the number of colonies of GKK2 is significantly greater than those of the other species. These results suggest that GKK2 are more bile-tolerant than other species, and thus more resistant to bile salt when passing through the gastrointestinal tract.

Heat Tolerance Test

Five species of strains, including GKK2, BCRC 17394 (purchased from the Bioresource Collection and Research Center at Taiwan Food Industry Research and Development Institute), *B. animalis* subsp. *Lactis* Bi 04 (deposited at the American Type Culture Collection, No. ATCC SD 5219), *B. animalis* subsp. *Lactis* BB-12 (deposited at the German Collection of Microorganisms and Cell Cultures, No. DSM 15954) and *B. animalis* subsp. *Lactis* Bi07 (deposited at the American Type Culture Collection, No. ATCC SD 5220) are used in this test. The strains are inoculated onto the MRS liquid culture media and heated at 70° C. for 5, 10 and 15 minutes. The colonies formed are then counted.

Figure 3:
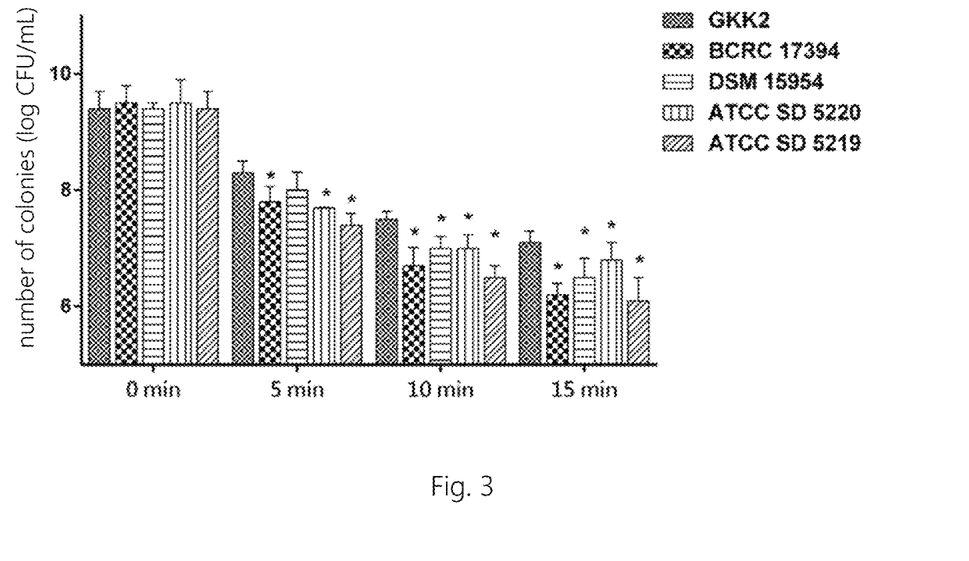
FIG. 3 shows the number of colonies after the heat tolerance test.

Results are shown in FIG. 3. The number of colonies of GKK2 and other four species all reached $5 \times 10^9$ cfu/ml before being heated (0 minute). On the other hand, the number of colonies of BCRC 17394, Bi04 and Bi07 are significantly lower than that of GKK2 after being heated for 5 minutes at 70° C. ($p<0.05$), while there is no statistically significant difference between the number of colonies of BB-12 and GKK2. The number of other four species are significantly lower than that of GKK2 after being heated for 15 minutes at 70° C. ($p<0.05$). As such, in a high-temperature environment, the number of colonies of GKK2 is significantly greater than those of other species. These results suggest that GKK2 are more heat-tolerant than other species. Given that lactic acid bacteria are typically not heat-tolerant and thus have to be stored at low temperatures to remain alive, these results further suggest that GKK2 are heat-tolerant and able to be stored at ambient temperature. Such features suggested that GKK2 are useful when present in products.

Bacterial Culture

Colonies are picked from the *Bifidobacterium lactis* mentioned above and then streaked onto a solid-state medium. In a preferred embodiment, the solid-state medium is MRS agar. Once fully grown, a single colony of *Bifidobacterium lactis* is inoculated into a flask containing a liquid medium for liquid culture. In a preferred embodiment, the *Bifidobacterium lactis* are cultured in a liquid medium at 35-50° C., in nitrogen or carbon dioxide of 0 to 1 vvm, and rotate at 10 to 100 rpm. In a preferred embodiment, the bacteria are cultured for 16 to 24 hours, more preferably for 18 hours. In a preferred embodiment, the liquid medium is MRS liquid medium. In a preferred embodiment, the ingredients of the liquid medium are shown in Table 1 below.

TABLE 1

| Ingredient | Percentage |
| --- | --- |
| Glucose | 1~10% |
| Yeast extract | 0.1~5% |
| Peptone | 0.1~5% |
| Trace element | 0.01~2% |
| Cysteine | 0.01~0.1% |
| Tween-80 | 0.05~1% |

Preparation of Freeze-Dried Powder

Once the lactic acid bacteria species is fully grown in liquid culture, the liquid media are centrifuged to obtain bacterial pellets. In a preferred embodiment, the liquid media are centrifuged at 1000 to 15000 rpm. The obtained bacterial pellets are mixed with a protecting agent (6-30% skimmed milk powder) and freeze-dried to be preserved at a low temperature. In a preferred embodiment, the temperature is set at −196 to −40° C. In a preferred embodiment, the mixture is freeze-dried for 16 to 72 hours. In a preferred embodiment, the freeze-dried mixture is preserved at −30 to 0° C. The freeze-dried powder of lactic acid bacteria is preserved to be used as an ingredient for the following cell experiments, that is, as one of the embodiments of the lactic acid bacteria active substance claimed by the present application. The embodiments of the lactic acid bacteria active substance claimed by the present application also include the liquid medium and the pellet as described above.

Experimental Animals and Experiment Design

The animals used in this experiment were 24 five-weeks-old male Balb/c mice purchased from the National Laboratory Animal Center. The mice were kept in an individual ventilated caging system located in a lab room for mice at the Laboratory Animal Service Center at China Medical University. The temperature in the animal facility was kept at 22±2° C., and the relative humidity at 40-60%. Light cycle was controlled by an automatic timer, with a dark period set from 07:00 to 19:00 and a light period set from 19:00 to 07:00. The animals were permitted free access to food and sterile reverse osmosis water, as well as 2 weeks of adaptation period before being used as subjects in this experiment.

Animal models of allergy used in animal experiments can be established using sensitization. In this experiment, allergens were used as antigens, and aluminum hydroxide as adjuvant. Allergens were administered subcutaneously to sensitize the animals. Blood was collected one week before and after the injection of allergens to confirm that the allergy model was successfully established by measuring the levels of antigen-specific antibodies in the serum isolated from the blood sample. Sensitization may be administered three to four times if necessary, so that the levels of antigen-specific antibodies in serum could be sufficient to meet the criteria of an allergy model required for subsequent tests. Sensitization to airway allergens is also established using spray, which causes the animals to inhale allergens into the respiratory tract to be in contact therewith.

Stimulation of allergies and asthma in mice using ovalbumin (OVA) is achieved based on an evenly mixed emulsion consisting of OVA (500 μg/ml) and incomplete Freund's adjuvant (OVA:IFA=1:1), wherein the emulsion is filtered using a sterile membrane filter before immediate use. The said allergen was administered subcutaneously to each group of mice on days 30, 40 and 50 of the experiment, and the 10-minute inhalation of 2% OVA allergen was administered by spray to each group on days 45 and 55 so that the allergic asthma can be induced.

24 five-weeks-old male Balb/c mice used in this experiment were divided into a control group that was fed with normal saline, a sensitized group that was sensitized with OVA, and two test groups that were sensitized with OVA and fed with high- and low-dose GKK2, respectively. There were a total of 4 groups with 6 mice per group. GKK2 was given to mice through tube-feeding, and the doses were converted from human to mice using a dose equivalent conversion factor of 12.3, which is calculated based on the ratio of the experimental animal's surface area to that of humans. The mice were weighed once a week. After the average weight of each group was obtained can then the daily doses for the mice be calculated, which is based on the daily doses of manufacturer's samples for adult humans (20 mg and 100 mg per day for a person of 60 kg body weight is equivalent to 10 and 30 billion colonies per day per person, respectively) using the following equation:

Daily feeding dose for mice(g)={dose for adult human/60kg(adult body weight)}×mice body weight(kg)×12.3(human-to-mice dose reduction factor)

The GKK2 doses to be fed to the test groups were calculated using the above equation and shown in Table 2:

TABLE 2

| Group | mg/kg |
|---|---|
| Low-dose GKK2 | 6.15 |
| High-dose GKK2 | 20.5 |

Figure 4:
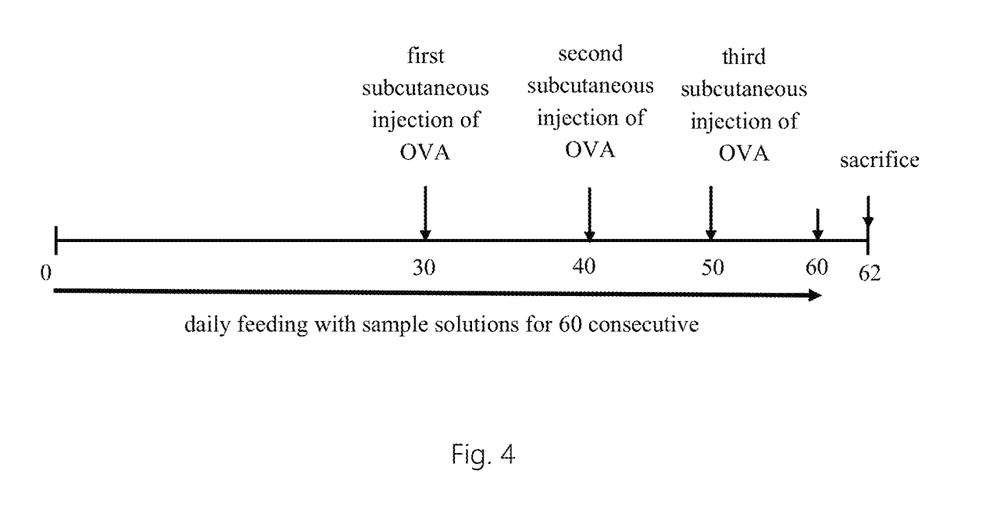
FIG. 4 shows the experimental procedures.

Samples to be fed to mice were made by adding GKK2 of the above doses in 0.9% saline. Stainless steel feeding tubes were normally immersed in 75% alcohol, and were taken out and rinsed using 0.9% saline before use. The needles were inserted into 1 ml sterile plastic syringes to serve as feeding tubes. The groups of mice were tube-fed with 0.2 ml saline (control group) or GKK2 solution of various concentrations, respectively. Each group was tube-fed daily with the above samples for 60 consecutive days. FIG. 4 depicts the general procedure of this experiment.

On day 62, all mice were sacrificed for blood samples and serum to be collected. Specifically, the blood sample was collected using a 1 ml syringe from the hepatic portal vein. Half of the whole blood samples were collected from the mice and placed into test tubes containing anti-coagulants for white blood cell classification and count. The other half whole blood samples were collected and placed into test tubes without anti-coagulants and incubated at ambient temperature for 1 hour. These samples were then centrifuged at 1000 rpm for 10 minutes, and the resulting supernatant was designated serum. Serum was stored at −80° C. for later analysis of immunoglobulins present in serum as well as allergen-induced specific antibodies.

Airway Resistance Test

One day before sacrifice, the non-invasive airway resistance of the mice were measured using the whole-body plethysmography (WBP, Buxco). This WBP allows a dynamic study of the breathing pattern and calculate the bronchoconstriction index in a unitless variable called enhanced Pause (Penh) using a specialized software. Generally, a higher Penh indicates a greater airway resistance. In this experiment, the mice were first placed inside the animal chamber and their baseline of Penh value was measured for 3 minutes. They were then exposed to nebulized 0.9% NaCl for 3 minutes, and their Penh value was then measured for another 3 minutes. Next, they were exposed for another 3 minutes to nebulized methacholine (6.25 mg/ml), a non-specific bronchoconstrictor, before their PenhMch was measured. The above steps were repeated using higher levels of methacholine (12.5 mg/ml, 25 mg/ml and 50 mg/ml). The results of this experiment were expressed in Penh ratio. Data analysis was conducted by dividing the PenhMch values obtained at each level of methacholine by PenhNaCl values of saline given to each subject.

Analysis of IgE Levels in Serum

IgE antibody levels in serum were determined using sandwich-ELISA. Various anti-mice monoclonal antibodies were mixed with a coating buffer (pH 9.6) individually at appropriate amounts. The resulting mixture was coated onto a Nunc-immuno 96-well plate and incubated for 1 hour. Unbound monoclonal antibodies were removed with wash buffer, and blocking buffer (200 μl/well) was added to the wells to block any remaining open binding sites. The plate was incubated for 30 minutes at room temperature and then washed with wash buffer. 100 μl mouse serum or IgE standards with a known concentration were added into the plate. After incubation for 1 hour, the plate was washed with wash buffer. Anti-IgE secondary antibodies conjugated to HRP were added at an appropriate level (100 μl/well). After incubation for 30 minutes at room temperature, the plate was washed with wash buffer. 100 μl TMB substrate was then added to react with HRP. After 15 minutes of color development. 100 μl 2N $H_2SO_4$ was added to stop the reaction with absorbance measured at 450 nm. Based on a Standard curve with IgE standards plotted against absorbance, the concentrations of antibodies in serum may be estimated by interpolation using a regression equation.

Analysis of Levels of Allergen-Induced Specific IgE in Serum

Levels of allergen-induced specific IgE antibodies in serum were determined using sandwich-ELISA. Various anti-mouse monoclonal antibodies were mixed with a coating buffer (pH 9.6) individually at appropriate amounts, and 100 μl/ml OVA antigens were then added. The resulting mixture was coated onto a Nunc-immuno 96-well plate and incubated for 1 hour. Unbound monoclonal antibodies were removed with wash buffer, and blocking buffer (200 μl/well) was added to the wells to block any remaining open binding sites. The plate was incubated for 30 minutes at room temperature and then washed with wash buffer. 100 μl mouse serum or IgE standards with a known concentration were added into the plate. After incubation for 1 hour, the plate was washed with wash buffer. Anti-IgE secondary antibodies conjugated to HRP were added at an appropriate level (100 μl/well). After incubation for 30 minutes at room temperature, the plate was washed with wash buffer. 100 μl TMB substrate was then added to react with HRP. After 15 minutes of color development. 100 μl 2N $H_2SO_4$ was added to stop the reaction with absorbance measured at 450 nm. Based on a Standard curve with IgE standards plotted against absorbance, the concentrations of allergen-induced specific antibodies in serum may be estimated by interpolation using a regression equation.

Tissue Sections

Airway tissues were embedded in paraffin and sectioned. The sections were then stained using Hematoxylin and eosin stain (H&E stain) and observed by microscopy.

Analysis of GSH Reductase Levels

A fixed amount of mouse liver was placed in HEPES buffer solution. Prior to the experiment, the samples should be stored at −80° C. for later analysis on GSH reductase. The analysis on the concentration thereof was conducted using commercially available ELISA.

Biostatistical Analysis

The results obtained from this experiment were expressed as mean±SD and were analyzed using SPSS 12.0 software. Differences between pairs of groups were measured using Duncan's Multiple Range test. P<0.05 indicates statistically significant difference. The results were plotted using SigmaPlot 10.0.

Results

Figure 5:
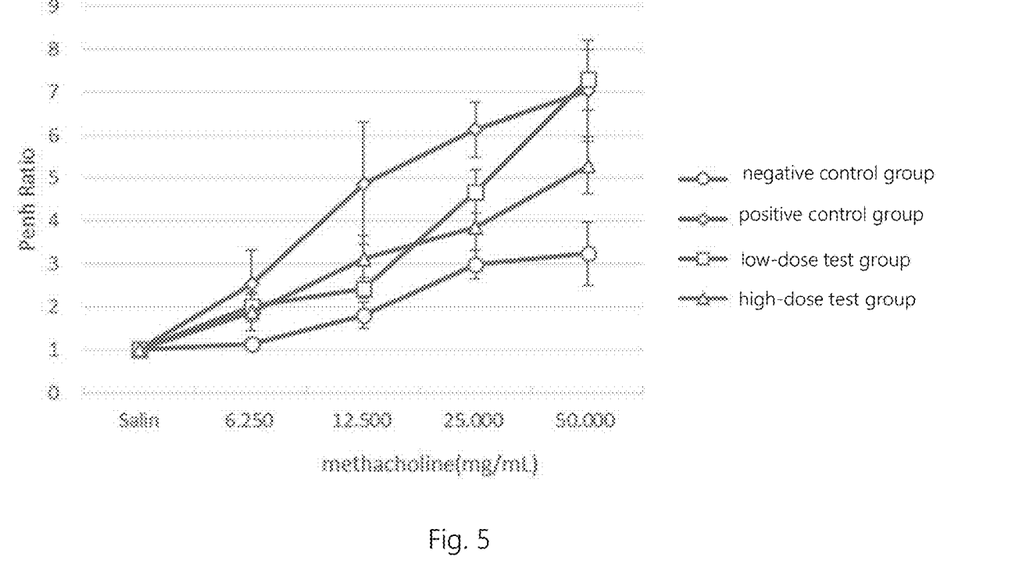
FIG. 5 shows the results of airway resistance test.

For the airway resistance tests, the results of each group are shown in Table 3 and the statistical analysis is shown in FIG. 5:

TABLE 3

| | Saline | Methacholine (mg) | | | |
| --- | --- | --- | --- | --- | --- |
| | | 6.250 | 12.500 | 25.000 | 50.000 |
| Control group | 1.000 | 1.147 | 1.807 | 2.984 | 3.243 |
| Sensitized group | 1.000 | 2.545 | 4.879 | 6.127 | 7.035 |
| Sensitized + low-dose GKK2 group | 1.000 | 2.003 | 2.448 | 4.694 | 7.290 |
| Sensitized + high-dose GKK2 group | 1.000 | 1.878 | 3.135 | 3.874 | 5.295 |

The above results showed that as the concentration of the nebulized bronchoconstrictor methacholine increased, the airway resistance in the sensitized group, to which OVA was administered intraperitoneally or by inhalation, increased significantly and eventually became significantly higher than that in the control group. As such, it was proved that an OVA-sensitized mouse model was successfully established. Moreover, even the concentration of the nebulized bronchoconstrictor methacholine increased, the airway resistance in the test groups where GKK2 was given did not increase as much as the sensitized group. Such result suggested that GKK2 administration may help lower the airway resistance induced by OVA allergens; in other words, the asthma-induced airway resistance may decrease. In addition, when given increased levels of GKK2, the test groups exhibited a smaller increase in the airway resistance. Such result suggested that therapeutic effects of GKK2 towards allergic asthma are concentration-dependent.

Figure 6:
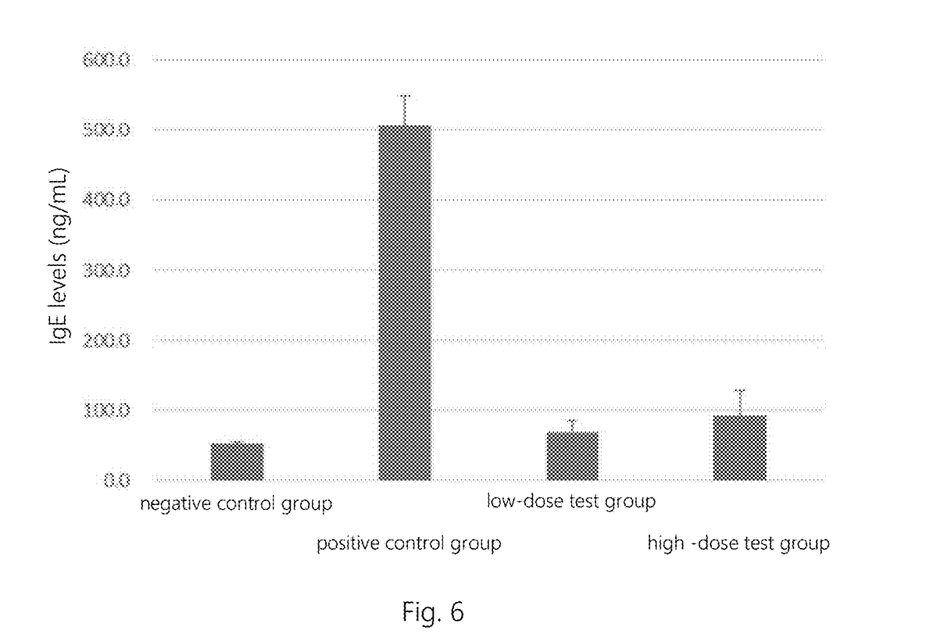
FIG. 6 shows the levels of non-specific IgE antibodies in serum.

For the concentrations of non-specific IgE antibodies in serum, the results are shown in Table 4 and the statistical analysis is shown in FIG. 6:

TABLE 4

| | Concentration (ng/ml) |
| --- | --- |
| Control group | 52.7 |
| Sensitized group | 507.2 |
| Sensitized + low-dose GKK2 group | 68.9 |
| Sensitized + high-dose GKK2 group | 91.9 |

In the sensitized mice (sensitized group), the concentrations of non-specific IgE antibodies in serum increased significantly when compared to those in the control group. In the sensitized mice that were tube-fed with GKK2 (high- and low-dose test groups), the concentrations of non-specific IgE antibodies in serum decreased significantly when compared to those in the sensitized group (p<0.05), and was eventually similar to that in the control group. Such results suggested that GKK2 administration may help lower the levels of non-specific IgE antibodies in serum and thereby improve allergic responses.

Figure 7:
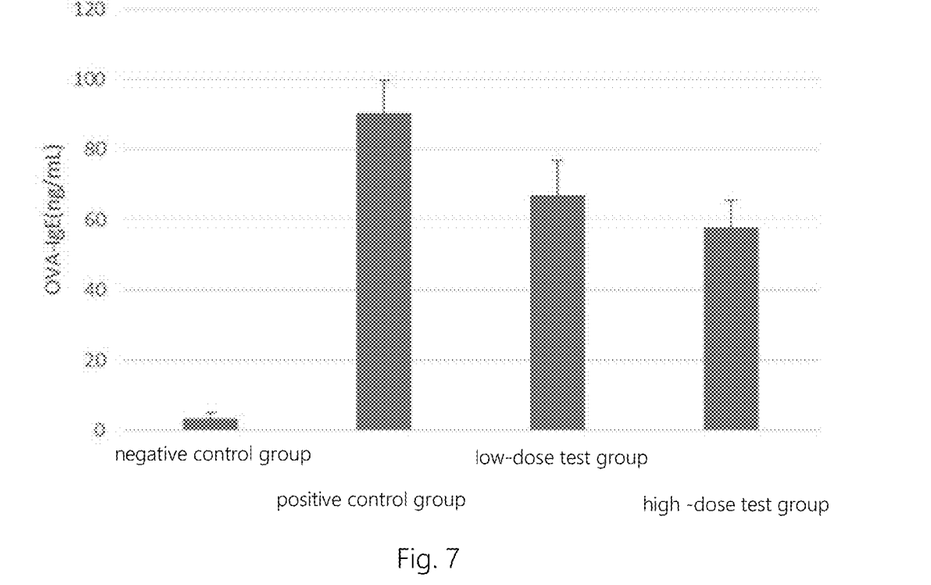
FIG. 7 shows the levels of specific IgE antibodies in serum.

For the concentrations of specific IgE antibodies in serum, the results are shown in Table 5 and the statistical analysis is shown in FIG. 7:

TABLE 5

| | Concentration (ng/ml) |
| --- | --- |
| Control group | 3.1 |
| Sensitized group | 90.5 |
| Sensitized + low-dose GKK2 group | 66.9 |
| Sensitized + high-dose GKK2 group | 57.7 |

In the sensitized mice (sensitized group), the concentrations of specific IgE antibodies in serum increased significantly when compared to those in the control group. In the sensitized mice that were tube-fed with GKK2 (high- and low-dose test groups), the concentrations of specific IgE antibodies in serum decreased significantly when compared to those in the sensitized group (p<0.05). Such results suggested that GKK2 administration may help lower the levels of specific IgE antibodies in serum and thereby improve allergic responses.

Figure 8:
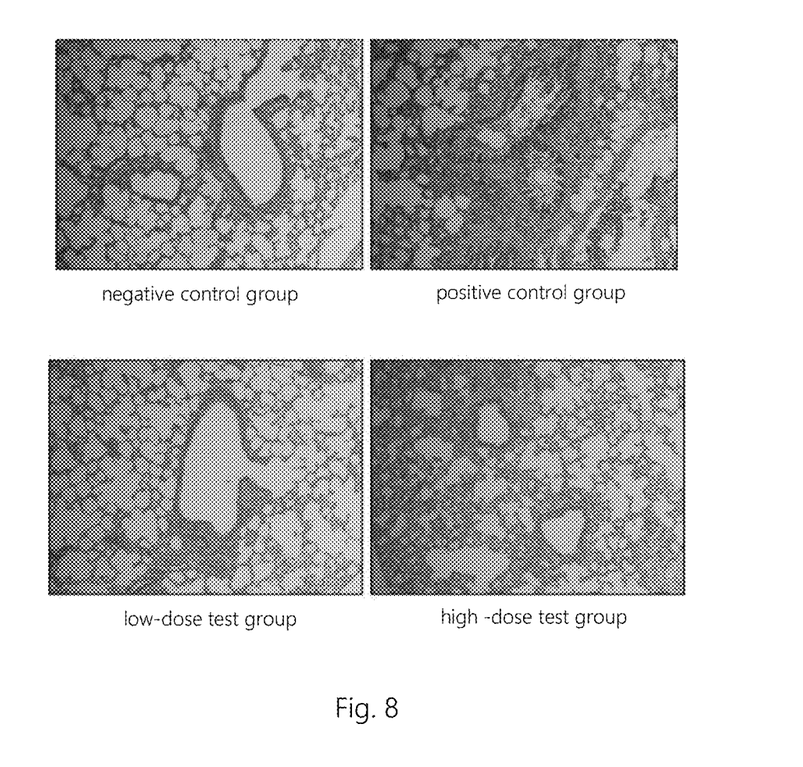
FIG. 8 shows airway tissue sections.

As for tissue sections, the results are shown in FIG. 8. In the sensitized mice (sensitized group), the airway diameters decreased significantly when compared to those in the control group. In the sensitized mice that were tube-fed with GKK2 (high- and low-dose test groups), bronchoconstriction occurred in a less obvious manner when compared to the sensitized group, and exhibited no significant difference when compared to the control group. Such results suggested that GKK2 administration may help alleviate bronchoconstriction and reduce the incidence of asthma.

Figure 9:
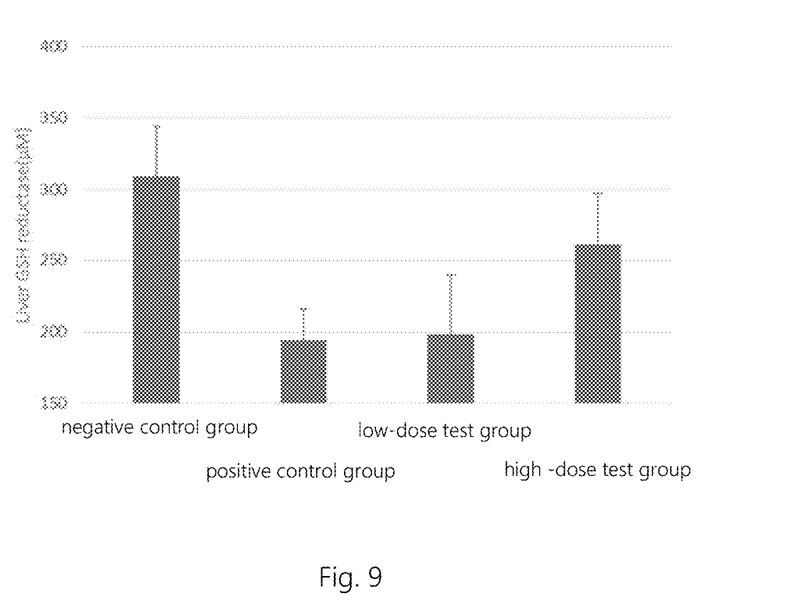
FIG. 9 shows the levels of GSH reductase.

For the concentrations of GSH reductase, the results are shown in Table 6 and the statistical analysis is shown in FIG. 9:

TABLE 6

| | Concentration (ng/ml) |
| --- | --- |
| Control group | 309.0 |
| Sensitized group | 194.8 |
| Sensitized + low-dose GKK2 group | 198.4 |
| Sensitized + high-dose GKK2 group | 261.2 |

In the sensitized mice (asthmatic group), the levels of GSH reductase decreased significantly. In the sensitized mice that were tube-fed with GKK2, the levels of GSH reductase increased significantly when compared to those in the asthmatic group (p<0.05). Such results suggested that GKK2 administration may help strengthen the immune system so as to lower an individual's susceptibility to allergic responses, thereby exhibiting therapeutic effects for reducing the incidence of asthma.

To sum up, it can be proved from the above test results that GKK2 is useful in alleviating bronchoconstriction triggered by allergic asthma, lowering the levels of allergy-induced non-specific and specific IgE antibodies in serum, and increasing the concentrations of GSH reductase in the body. Hence, *Bifidobacterium Lactis* GKK2 is useful in improving allergic asthma.

The present invention provides a composition, which comprises GKK2 and can help alleviate allergic responses.

The composition further comprises an additive. In a preferred embodiment, the composition can be an excipient, preservative, diluent, filler, absorption enhancer, sweetener or a combination thereof. The excipient can be selected from sodium citrate, calcium carbonate, calcium phosphate, sucrose or a combination thereof. The preservative, such as benzyl alcohol and parabens, can prolong the shelf life of pharmaceutical compositions. The diluent can be selected from water, ethanol, propylene glycol, glycerol or a combination thereof. The filler can be selected from lactose, high molecular weight polyethylene glycol or a combination thereof. The absorption enhancer can be selected from dimethyl sulfoxide (DMSO), laurocapram, propylene glycol, glycerol, polyethylene glycol or a combination thereof. The sweetener can be selected from Acesulfame K, aspartame, saccharin, sucralose, neotame or a combination thereof. In addition to the additives listed above, other ones may be selected according to actual needs provided that the pharmaceutical effects of the lactic acid bacteria active substance are not affected.

The composition can be developed into various products in the pharmaceutical industry. In a preferred embodiment, the composition is a drug, feed, drink, nutritional supplement, dairy product or health food.

The composition can take various forms to meet the subject's needs. In a preferred embodiment, the composition can be in powder, tablet, granule, suppository, microcapsule, ampoule/ampule, liquid spray or suppository form.

The composition of the present invention can be administered to an animal or a human. Provided that the effects of the lactic acid bacteria active substance are not affected, it can be made into any dosage forms and administered via an appropriate route to the animal or human depending on the dosage form.

Preparation of Composition

When GKK2 of the present invention is of dietary use, the embodiment regarding composition 1 as described below shall be illustrative.

Composition 1: Freeze-dried powder of GKK2 was used as lactic acid bacteria active substance (20 wt %), and was well-mixed with benzyl alcohol used as a preservative (8 wt %) and glycerol used as a diluent (7 wt %). The resulting mixture was dissolved in pure water (65 wt %) and stored at 4° C. for future use. The notation "wt %" refers to the proportion of the weight of each ingredient relative to the total weight of the composition.

When GKK2 of the present invention is of medical use, the embodiment regarding composition 2 as described below shall be illustrative.

Composition 2: Freeze-dried powder of GKK2 was used as lactic acid bacteria active substance (20 wt %), and was well-mixed with benzyl alcohol used as a preservative (8 wt %), glycerol used as a diluent (7 wt %), and sucrose used as a diluent (10 wt %). The resulting mixture was dissolved in pure water (55 wt %) and stored at 4° C. for future use. The notation "wt %" refers to the proportion of the weight of each ingredient relative to the total weight of the composition.

Deposit number of lactic acid bacteria I (GKK2): CGMCC No. 15205

What is claimed is:

1. A method of improving airway constriction caused by airborne allergic asthma introduced by respiratory tract comprising:
   administering a composition comprising a *Bifidobacterium lactis* of an effective amount of 20-100 mg/60 kg body weight to a subject in need thereof,
   wherein the *Bifidobacterium lactis* is GKK2, deposited as CGMCC No. 15205 at China General Microbiological Culture Collection Center.

2. The method of claim 1, wherein the *Bifidobacterium lactis* GKK2 is acid-tolerant, bile-tolerant and/or heat-tolerant, wherein the colony forming unit per milliliter is about $5\times10^8$ cfu/ml in a culture medium at pH 3.2 to 2.0, about $5\times10^9$ cfu/ml in a liquid culture mixed with 0.3% bile salt, and/or $5\times10^7$ to $5\times10^9$ cfu/ml in a heated liquid culture.

3. The method of claim 1, wherein the *Bifidobacterium lactis* GKK2 is prepared by the following method:
   (a) streaking the *Bifidobacterium lactis* GKK2 on a solid-state medium to obtain single colonies; and
   (b) inoculating a single colony of the *Bifidobacterium lactis* GKK2 cultured at step (a) to a liquid culture for liquid-state culture.

4. The method of claim 3, wherein the said method further comprises the following steps:
   (c) centrifuging the liquid culture cultured at step (b) to obtain a bacterial pellet; and
   (d) freeze-drying the bacterial pellet obtained at step (c).

5. The method of claim 3, wherein step (b) is carried out at 30 to 50° C., in nitrogen or carbon dioxide of 0 to 1 vvm, rotate at 10 to 100 rpm, and/or incubate for 16 to 24 hours.

6. The method of claim 4, wherein a temperature for the freeze-drying at step (d) is −196 to −40° C.

7. The method of claim 1, wherein the composition further comprises an additive selected from the group consisting of an excipient, preservative, diluent, filler, absorption enhancer, sweetener and a combination thereof.

8. The method of claim 1, wherein the composition is formulated as a drug, feed, drink, nutritional supplement, dairy product or health food.

9. The method of claim 1, wherein the composition is in a form of a powder, tablet, granule, suppository, microcapsule, ampoule/ampule, liquid spray or suppository form.

10. The method of claim 1, wherein, after administering *Bifidobacterium lactis* GKK2 to the subject in need thereof, the subject exhibits lower airway resistance than a subject not administered *Bifidobacterium lactis* GKK2.

11. The method of claim 1, wherein, after administering *Bifidobacterium lactis* GKK2 to the subject in need thereof, the subject exhibits reduced levels of non-specific IgE antibodies in serum than a subject not administered *Bifidobacterium lactis* GKK2.

12. The method of claim 1, wherein, after administering *Bifidobacterium lactis* GKK2 to the subject in need thereof, the subject exhibits reduced levels of specific IgE antibodies in serum than a subject not administered *Bifidobacterium lactis* GKK2.

13. The method of claim 1, wherein, after administering *Bifidobacterium lactis* GKK2 to the subject in need thereof, the subject exhibits less bronchoconstriction than a subject not administered *Bifidobacterium lactis* GKK2.

14. The method of claim 1, wherein, after administering *Bifidobacterium lactis* GKK2 to the subject in need thereof, the subject exhibits increased levels of GSH reductase in liver tissue interstitial fluid than a subject not administered *Bifidobacterium lactis* GKK2.

* * * * *